United States Patent [19]

Hunter

[11] Patent Number: 5,397,297
[45] Date of Patent: Mar. 14, 1995

[54] ADHESIVE BANDAGE WITH IMPROVED APPLICATION SYSTEM

[76] Inventor: Theodore K. Hunter, 501 Riverside St., Paso Robles, Calif. 93446

[21] Appl. No.: 202,995

[22] Filed: Feb. 28, 1994

[51] Int. Cl.⁶ ............................................. A61F 13/00
[52] U.S. Cl. ..................................... 602/54; 602/57; 206/440
[58] Field of Search ...................... 206/438, 440–441; 602/41–59

[56] References Cited

U.S. PATENT DOCUMENTS

| | | | |
|---|---|---|---|
| 2,880,863 | 4/1959 | Stanton | 206/441 |
| 2,889,039 | 6/1959 | Schladermundt et al. | 206/441 |
| 2,973,859 | 3/1961 | Schladermundt et al. | 206/441 |
| 3,899,077 | 8/1975 | Spiegelberg | 206/441 |
| 4,913,138 | 4/1990 | Yoshida et al. | 206/441 X |
| 4,915,228 | 4/1990 | Johns | 206/441 |
| 5,052,381 | 10/1991 | Gilbert | 128/155 |
| 5,099,832 | 3/1992 | Ward | 206/441 X |
| 5,275,284 | 1/1994 | Onotsky | 206/441 |

*Primary Examiner*—Robert A. Hafer
*Assistant Examiner*—Brian E. Hanlon
*Attorney, Agent, or Firm*—Basil Travis

[57] ABSTRACT

An adhesive bandage having essentially flat, planar structural components and including a system to facilitate simplified application of the bandage over a wound on the human skin by providing pairs of release strips folded back across themselves to furnish end members sealed within respective ends of a package so that when the package is opened a release strip is simultaneously pulled away from an adhesive coating of a bandage film thereby further allowing its application with only one hand when necessary.

2 Claims, 4 Drawing Sheets

ADHESIVE BANDAGE WITH IMPROVED APPLICATION SYSTEM

BACKGROUND OF THE INVENTION

1. Field of Invention

This invention relates to thin flexible adhesive bandages and their application to wounds on the human skin.

More specifically, the present invention concerns a particular structural arrangement of common bandage components to provide an improved system for removing a bandage from its packaging and then applying the bandage to a wound on the skin.

2. Prior Art

A most thorough discussion of wound dressings has been recently provided by Gilbert in his U.S. Pat. No. 5,052,381 (1991), and it would be redundant to repeat a historical review of prior art and improvements to bandages in light of the enormity of what has already been said, with a possible exception of merely recognizing here that there are known in the prior art numerous application systems for many bandages which utilize common components but are distinguished by their particular constructional arrangements which in turn control how the bandage is used.

For example, in U.S. Pat. No. 5,052,381 (1991), Gilbert provides embodiments of his bandage, which need be distinguished both structurally and in their application from the present invention. In one embodiment, Gilbert describes an adhesive film having two release sheets, one of shorter length than the other, but each strippably adhered to an adhesive coating on a bandage film, and the shorter sheet folded back a short distance to form a tab. An end of the longer sheet overlies said gripping tab to form a second tab whereby both tabs may be simultaneously pulled by the fingers to partially strip away the release sheets while also manipulating the bandage for uniform application over a wound. In another embodiment both tabs are folded back, but in either case the release sheets of Gilbert are not folded back completely across their inner layers to extend beyond the ends of the bandage so as to provide pull tabs within ends of the package. Further, the bandages of Gilbert must first be physically removed from their packages before pulling their tabs to apply them, while in contrast the bandage of the present invention provides for removal of a release sheet simultaneously with removal of its package thereby allowing application of the bandage by a small adhering tab with only one hand when required.

Another bandage which should be distinguished is described by Johns in U.S. Pat. No. 4,915,228 (1990) where its package is said to act as means for application to a skin area with opening of the package in a single step. Although the backing sheets of Johns are stripped away from his bandage along with the package, the arrangement of the bandage is structurally different from that of the present invention because Johns' bandage is folded within its package, with adhesive facing out and in contact with a strippable backing layer attached to the package interior so that when the package is opened by spreading open its halves, the adhesive of the bandage is exposed for placement on the skin as the package is pulled apart. This application necessarily requires the use of two hands, as should be further distinguished from the present invention which may allow its application by the use of only one hand.

Other bandage systems having common structural components are known as in U.S. Pat. Nos. 4,928,680 and 4,917,929, but they also do not provide the advantages of the present invention.

Accordingly, it is a general object of the present invention to provide a structural composition of a bandage and its component parts which allow virtual complete removal of its package and protective backing strips in a single step thereby furnishing a bandage with an exposed adhesive layer for simplified application to a wound on the human skin with only one hand. This objective is achieved in the present invention.

SUMMARY OF THE INVENTION

A flexible adhesive bandage of essentially flat rectangular planar configuration is provided as comprising an elastomeric film having a front and rear surface. The front surface of the film is coated with a pressure sensitive adhesive upon which there is positioned a central pad for placement upon a wound area on the human skin. A pair of folded thin plastic release strips, one of short length and one of longer length, completely cover the adhesive coating with their inner layers, the longer, said inner layer, also crossing over and covering a central pad, providing respective folds of both short and long inner layers meeting on a fold line at one end of the film so that the outer layers of the release strips are folded back across their inner layers to extend beyond the ends of the film thereby resulting in end members. Enclosing the said components of the bandage is an essentially flat rectangular protective package consisting of two larger planar paper halves, but sealed to each other with contact adhesive outside the periphery of the film wherein the contact adhesive also fastens the end members of said outer release strip layers to their respective longitudinal ends of the package. A margin on the package between an end and a margin limit line comprises a tab provided by the margin area for pulling with the human fingers and opening the package by simply pulling it apart along its longitudinal axis, and because the margin limit line is co-axially parallel with the fold line on the film, the act of opening the package causes simultaneously stripping the entire longer release strip along with virtually the entire package away from the bandage thereby freeing the bandage with its exposed adhesive for application to and only by fingers holding the tab, said tab then subsequently being pulled away contemporaneously with application of the bandage to the skin with need of only one hand.

DETAILED DESCRIPTION OF THE PREFERRED EMBODIMENT

Before turning to the drawings, it might be briefly said that those skilled in the art may agree that there are some instances where it is very difficult for one to apply a bandage to oneself by using both hands. This is especially true where one hand is injured and the bandage need be applied to the injured hand. Moreover, in an emergency there isn't always time to read complicated directions for using various known shapes and sizes of bandages, and although this preferred embodiment may particularly refer to bandages of rectangular configuration, any and all reference to such bandages should be understood to also encompass bandages of different planar structural configurations, such as square, oval and round, but wherein their linear components compliment each other within the scope and spirit of this disclosure to provide simplified application of the bandage to a wound area of the skin by use of one hand when necessary.

Figure 1:
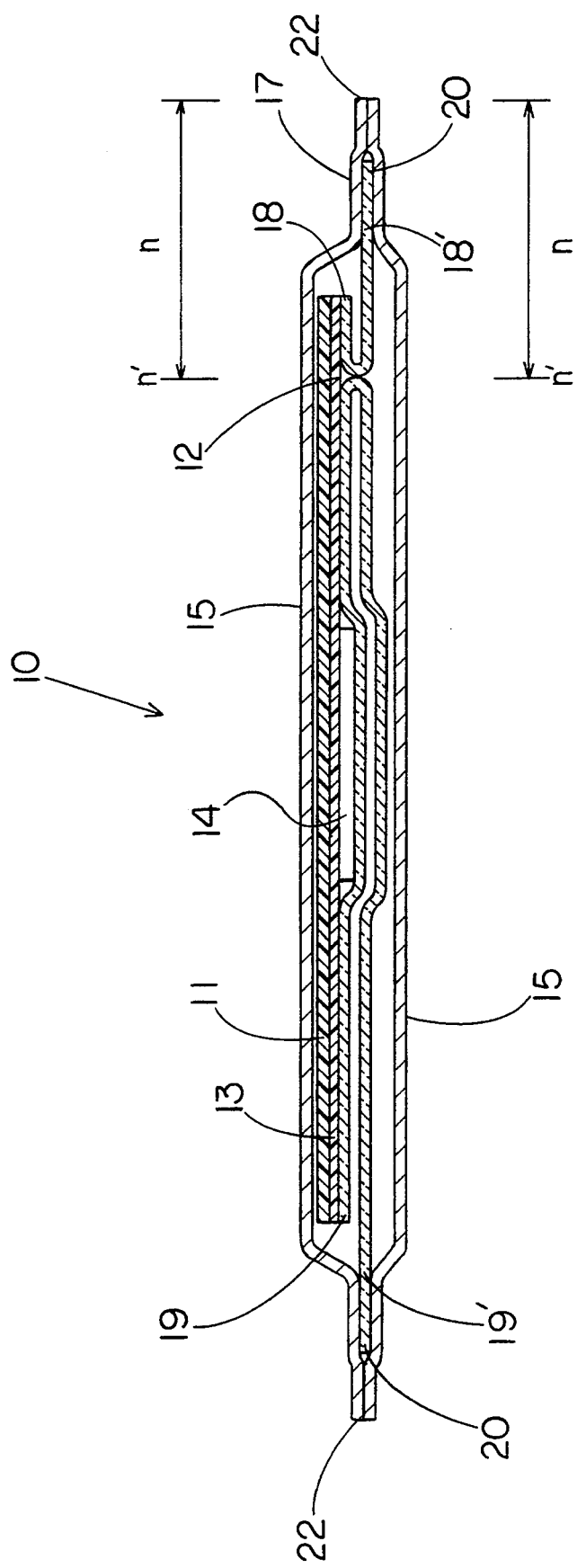
FIG. 1 is a cross-sectional view showing the present invention's longitudinal components within their package.

With these introductory remarks in mind, and now turning to the drawings, FIG. 1 is a cross-sectional view of a bandage and its essentially flat, planar structural components 10 of the present invention illustrating their longitudinal layered components within a package 15 prior to use. The package 15 preferably consists of two essentially flat planar paper halves having parallel margin areas n at one end 22 of their linear length which provides a tab 17 between a notch 16 on its periphery edge 23' (see FIG. 2) and congruent with a margin limit line n' of the package, said notch 16 (see FIG. 2) defining the limit line n' of the margin n and also a boundary of the tab 17 of the package 15.

Enclosed within the package 15 is an essentially flat, flexible planar elastomeric film 11 with a pressure-sensitive coating 13 on one surface and central pad 14 thereon, said pad preferably of gauze for placement upon a wound and attached thereto by the adhesive coating 13 of the elastomeric film 11. Two release strips, preferably of 0.5 mil polyethylene, completely but releasably cover the adhesive coating 13 by inner layers 18 and 19, the longer of which 19 also crossing over and covering the central pad 14, and each said release strip folded back across its respective inner layer to provide an outer layer 18' and 19' with their folds meeting upon a fold line 12 of the elastomeric film 11 which is congruent to and co-axially parallel with the package notch 16 (see FIG. 2) on the margin limit line n' of the package.

Figure 4:
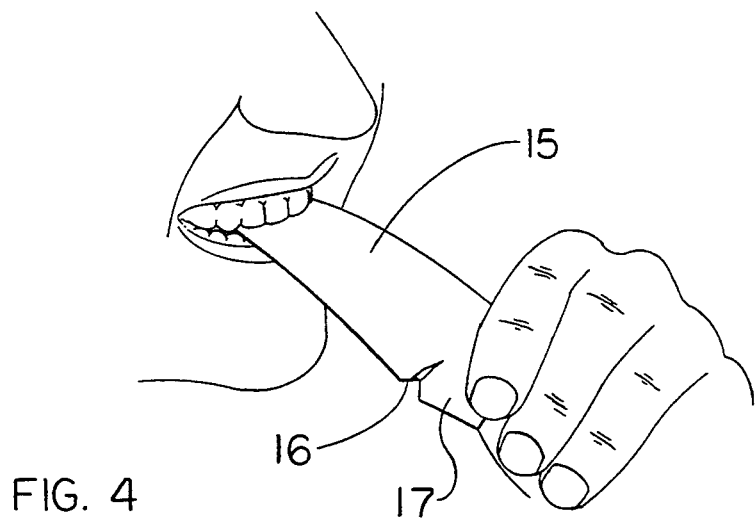
FIG. 4 is a perspective view showing an alternative method of opening the package with one hand.
Figure 5:
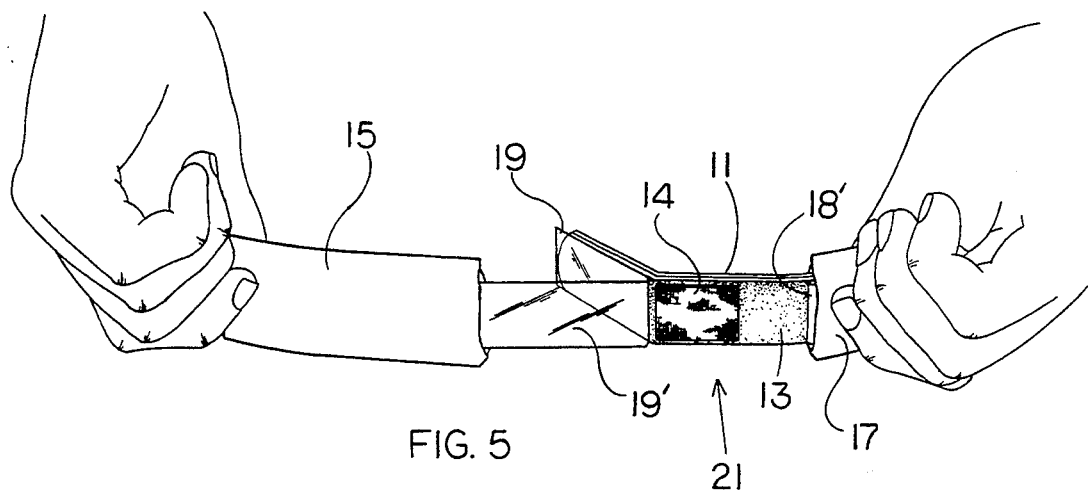
FIG. 5 is a perspective view of the front surface of the film and internal structural components of the bandage as the package is being opened.
Figure 6:
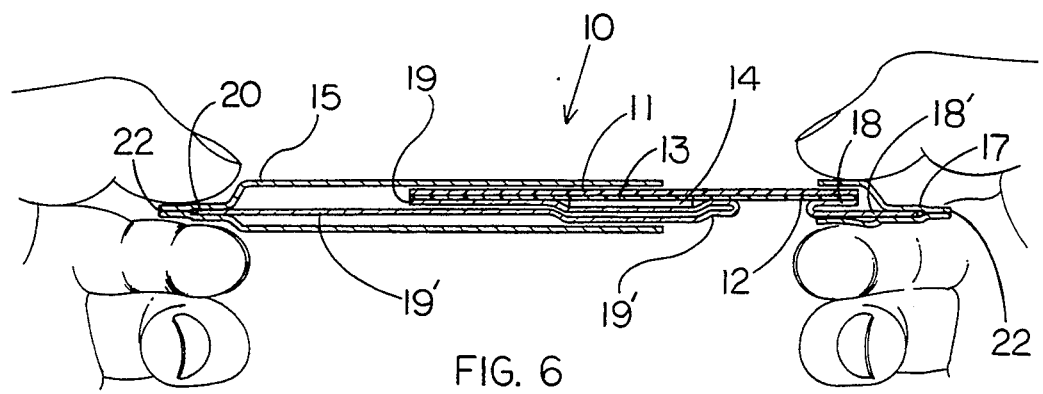
FIG. 6 is a cross-sectional view illustrating the longitudinal components of the bandage as the package is being opened.

The outer layers of each release strip, one short 18' and one long 19', are completely folded back across their inner layers 18 and 19 to provide end members 20 which extend beyond ends of the elastomeric film 11 and are sealed into respective ends 22 of the package 15 so that when the package is pulled apart lengthwise as illustrated in FIGS. 2–6, the tab 17 being compressed between a thumb and forefinger, as shown in FIG. 6, grips both the outer layer 18' and inner layer 18 of said short release strip and also an end of said film 11 to allow stripping of both layers of the longer release strip 19' and 19 away from the adhesive coating 13 along with a major portion of the package 15 to free the bandage for application.

Figure 2:
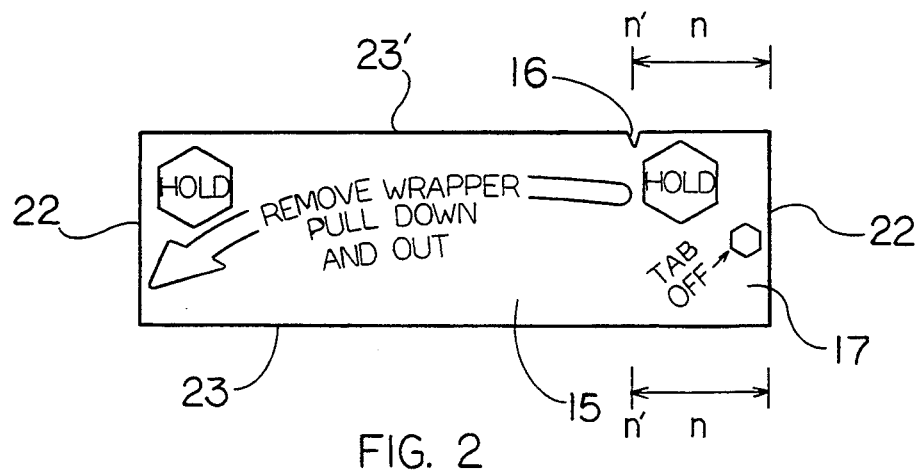
FIG. 2 is a plan view of one side of the package.

FIG. 2 shows one preferred embodiment of outer package 15 design illustrating directions for opening it with respect to a position of a wedged shaped notch 16 in the periphery edge 23' of said package, said notch 16 congruent with a margin limit line n' of margin n which also comprises a boundary for tab 17. It is obviously understood that FIG. 2 illustrates a surface of only one of a pair of identical flat planar paper halves having ends 22 and edges 23 and 23' in preferred rectangular configuration, however said ends and edges may be indistinguishable where the package 15 is of other planar shapes such as square or round. Furthermore, it should be pointed out that although an opposite side of FIG. 2 is not particularly illustrated nor described, it must necessarily be present as a mirror image (with or without instructions thereon) to form a package 15 (see FIGS. 1 and 6), but because of asymmetrical positioning of the notch 16 thereon, said reverse side would also provide means for interchangeable opening of said package 15 other than by grasping tab 17 with a right hand, while the reverse side (a mirror image) would provide the same tab 17 for grasping with a left hand. This feature is believed yet another advantage of the present invention, however, such mechanical utilization of asymmetry is obviously elementary and need not be further discussed nor claimed herein.

Figure 3:
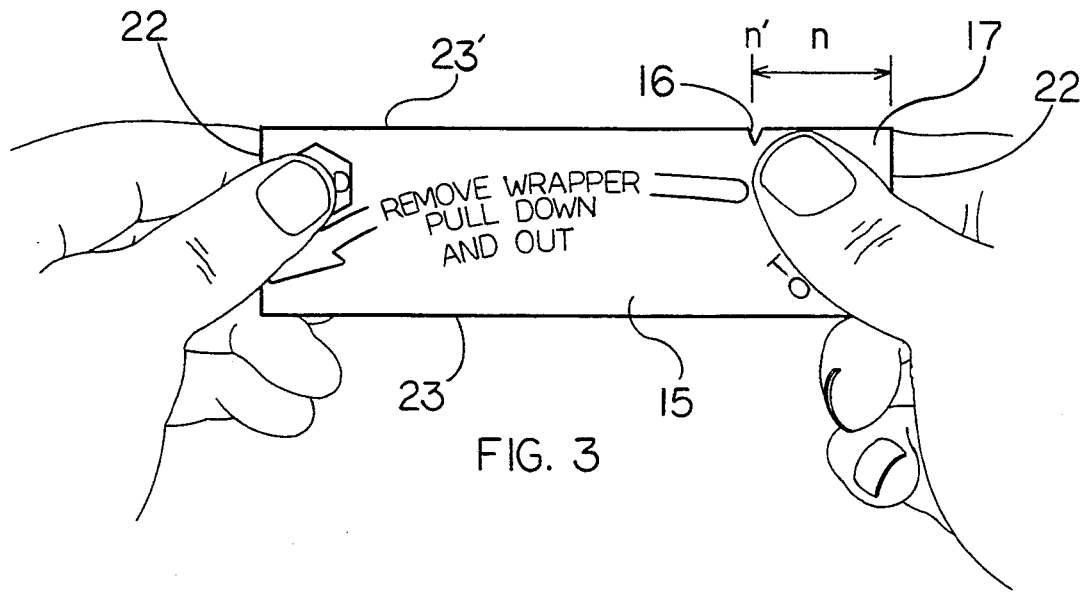
FIG. 3 is a plan view illustrating one method of opening the package with two hands.

FIG. 3 illustrates one preferred method of opening the package 15 in accordance with the instructions shown in FIG. 2. It should be emphasized that grasping the preferred illustrated position of tab 17 is slightly more inward towards the notch 16 than the opposite grasping position being closer to its respective edge 22, however both grasping positions are proximate to and parallel with a longitudinal periphery edge 23' of the package 15 so that when the package is pulled apart longitudinally, the notch 16 in the periphery edge 23' causes a tearing of both halves of the package essentially along the margin limit line n'.

FIG. 4 illustrates an alternative way of opening the package 15 with use of only one hand which is believed to be another advantage of the present invention since it is not always possible to use both hands when opening a bandage, especially when one hand is injured. However, it should be further pointed out here that either hand may be used to grasp and pull the tab 17 and it is not critical whether the package is upside down or not as long as the user understands that an essentially free adhesive bandage film 11 will be preferably removed from the package with the tab for application to a wound.

FIG. 5 shows the next step of pulling the package 15 apart as was begun in FIG. 3 using both hands. In FIG. 5, a front surface 21 of the elastomeric film 11 is illustrated, which within its package may have been perceived as its rear side with respect to consistent hand orientation in FIGS. 3, 6, 7, and 8, but the figure is illustratively turned over here in FIG. 5 to exhibit and teach how the opening mechanism works. Of course, it should be recognized that it is not critical for the front surface 21 of the film 11 to face in an opposite planar direction as any package instruction, since similar instructions might as well be printed on both exterior planar surfaces of the package. But as shown in FIG. 5, it is only necessary for fingers of one hand to firmly grasp the tab 17 while an opposite linear end 22 of the package is pulled away from the tab 17, by any means (even the teeth of FIG. 4) thereby stripping a longer outer layer of a plastic release strip 19', along with its inner layer 19, away from an adhesive coating 13 and pad 14 on the elastomeric film 11, along with virtually all of the package 15 to expose said film 11 for application.

In order to more precisely teach its internal unlocking mechanism, a cross-sectional elevational view of the bandage and its components 10 of the present invention is shown in FIG. 6, as said bandage is being opened by being pulled apart. It can been seen that FIG. 6 is a similar view of FIG. 1, with an exception as displayed in FIG. 6, that the long outer plastic release strip 19' has been pulled away from the fold line 12 of the film 11 by its end member 20 along with the end 22 of the package 15, while the fold connecting short plastic release strips 18 and 18' remains at the fold line 12. This particular mechanical mechanism is believed a unique feature of the bandage and its components 10 which is made possible by grasping tab 17 as shown in FIG. 3, and according to positions shown in FIG. 2, so that tab 17 is compressed by the fingers in FIG. 6 thereby squeezing planar components within said tab 17 together to permit sliding removal of the package 15, along with the longer release strips 19 and 19' by simply pulling them apart from the tab 17.

Figure 7:
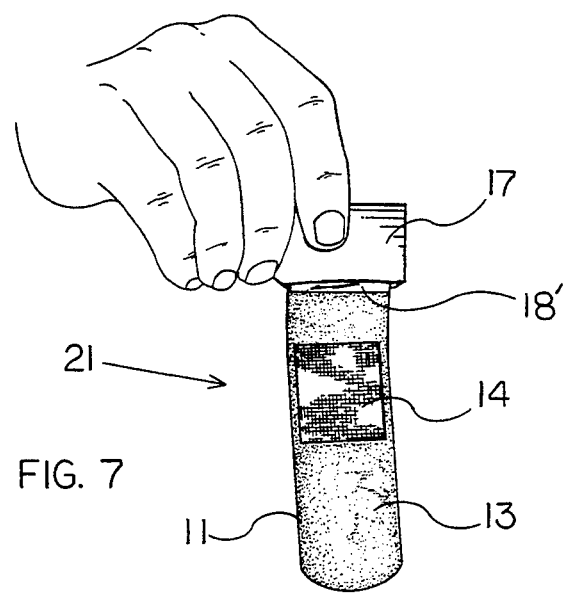
FIG. 7 illustrates a free adhesive bandage held by its tab just prior to application using only one hand.

Once the package 15 with long release strips 19 and 19' is removed as shown in FIG. 7, the free adhesive film 11, as displaying its front side or surface 21 with exposed adhesive coating 13 and pad 14, is merely suspended by gravity from the hand which pulled the tab 17 in any of FIGS. 3–7, said adhesive being ready for contact with the skin area where it will become anchored thereto.

Figure 8:
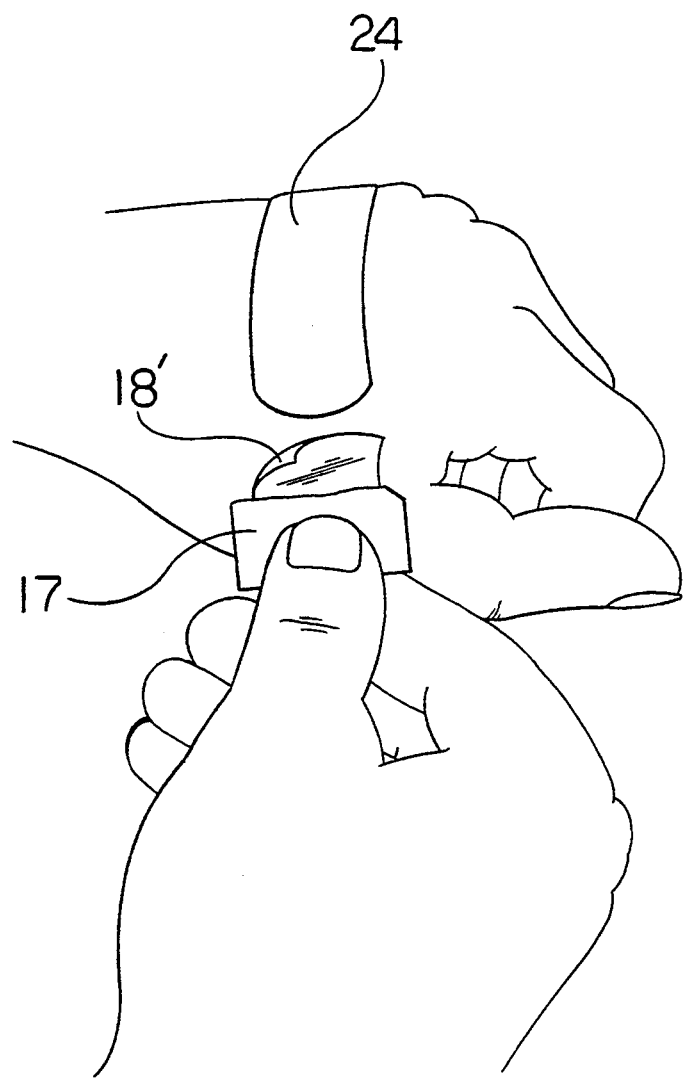
FIG. 8 shows application of a bandage to the human skin as the tab, along with its short release strip, is being pulled away.

FIG. 8 illustrates the rear surface 24 of the film 11 upon application of the front surface 21 as shown in FIG. 7, to the skin by simply pulling the tab 17 away and thereby also pulling away from the adhesive coating 13 the short plastic release strip 18' layer.

As one final thought, those skilled in the art may observe that the present invention was introduced to provide an improved application system for ease of applying an adhesive bandage without necessity of performing complicated manipulations or having to read complicated directions during an emergency or in the dark, so a natural question that follows is what happens if the directions as illustrated in FIGS. 2–8 are not followed. In other words, what would be the result if a user inadvertently removed tab 17 first? The answer is nothing, since the bandage would be applied in reverse order. That is to say if the tab 17 was removed first, there would be exposed its enclosed adhesive coating 13 for anchoring upon the skin with subsequent application of the elastomeric film 11 by simply removing by pulling the opposite end 22 of the package 15, instead of the tab 17, across a wound area, thusly providing one final advantage of the present invention.

Having described my invention in detail,
I claim:

1. A bandage having essentially flat, planar structural components a protective package, and a system to facilitate simplified application of the bandage over a wound on the human skin which comprises:

(A) an elastomeric film having an essentially flat planar front and rear surface of rectangular configuration with length greater than width and ends, said film having a margin area with margin limit line near one end of its length defining a fold line the margin limit line;
 (i) a pressure-sensitive adhesive coating on the front surface of the film;
 (ii) a central pad on the adhesive coated front surface of the film for placement upon a wound area on the human skin;

(B) said protective package enclosing said structural components and said system, said package comprising a pair of paper layers releasably sealed to each other with contact adhesive outside the periphery of the film, said package having a notch congruent with the margin limit line, and said margin area also defining a tab for grasping and pulling by the human fingers to open the package;

(C) a pair of folded thin plastic release strips, one of said pair of strips being a short strip and the other of said pair of strips being a long strip, each strip folded to provide both a inner and outer layer with their respective folds meeting upon the fold line of the film;
 (i) the inner layers of each release strip releasably covering the adhesive coating of the film, but the longer strip also crossing over and covering the central pad;
 (ii) the outer layers of each release strip being folded back across their inner layers thereby providing end members which extend beyond the ends of the film and into sealed ends of the protective package, so that when the package is opened;
  (a) the longer plastic release strip is stripped from the adhesive coating on the film and removed from the bandage with a major portion of the package;
  (b) the short plastic release strip remains affixed to the adhesive on the film for application of the bandage to a wound on the human skin, and the subsequent release of said short strip with the tab and remnants of the package from the adhesive coating on the film is achieved by further pulling the tab with the fingers.

2. The bandage of claim 1 wherein the pair of thin plastic release strips are polyethylene.

* * * * *